United States Patent [19]

Aldrovandi et al.

[11] Patent Number: 4,702,675
[45] Date of Patent: Oct. 27, 1987

[54] PERISTALTIC PUMP PROVIDED WITH A PRESSURE MEASUREMENT DEVICE

[75] Inventors: Mauro Aldrovandi, Mirandola; Domenico Cianciavicchia, Teramo; Renato Pedrazzi, Mirandola, all of Italy

[73] Assignee: Hospal A.G., Meyzieu, France

[21] Appl. No.: 761,933

[22] Filed: Aug. 2, 1985

[30] Foreign Application Priority Data

Aug. 7, 1984 [IT] Italy ................................. 53709/84[U]

[51] Int. Cl.⁴ ............................................. F04B 43/12
[52] U.S. Cl. ........................................ 417/63; 73/730; 417/477
[58] Field of Search ............... 417/474, 475, 476, 477, 417/63, 43; 73/730; 340/626

[56] References Cited

U.S. PATENT DOCUMENTS

| | | | |
|---|---|---|---|
| 3,799,702 | 3/1974 | Weishaar | 417/477 X |
| 4,120,033 | 10/1978 | Corso et al. | 417/63 X |
| 4,227,420 | 10/1980 | Lamadrid | 73/730 X |
| 4,236,880 | 12/1980 | Archbald | 417/63 X |
| 4,278,085 | 7/1981 | Shim | 417/477 X |
| 4,468,170 | 8/1984 | Hanset | 417/63 X |

Primary Examiner—Leonard E. Smith
Attorney, Agent, or Firm—Gerald D. Sharkin; Robert S. Honor; Walter F. Jewell

[57] ABSTRACT

Apparatus for circulating a liquid along a tubular conduit comprises a peristaltic pump provided with a rotor which acts through the intermediary of rollers, on an elastically deformable tube disposed in series along the mentioned tubular conduit and a device mounted outside on a section of the deformable tube for emitting an electric signal depending on the deformation induced in operation in the section of tube by the pressure of the said pumped liquid.

4 Claims, 9 Drawing Figures

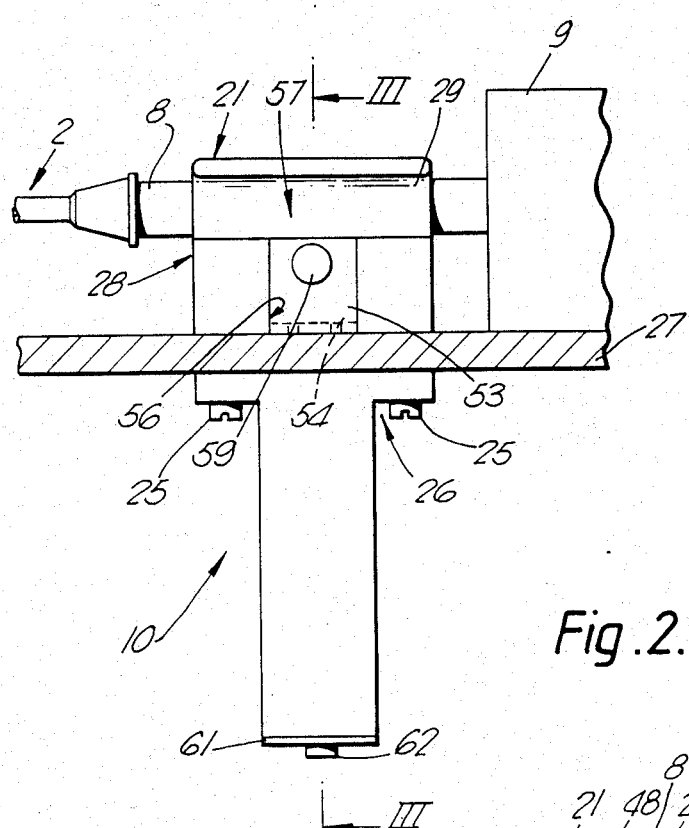
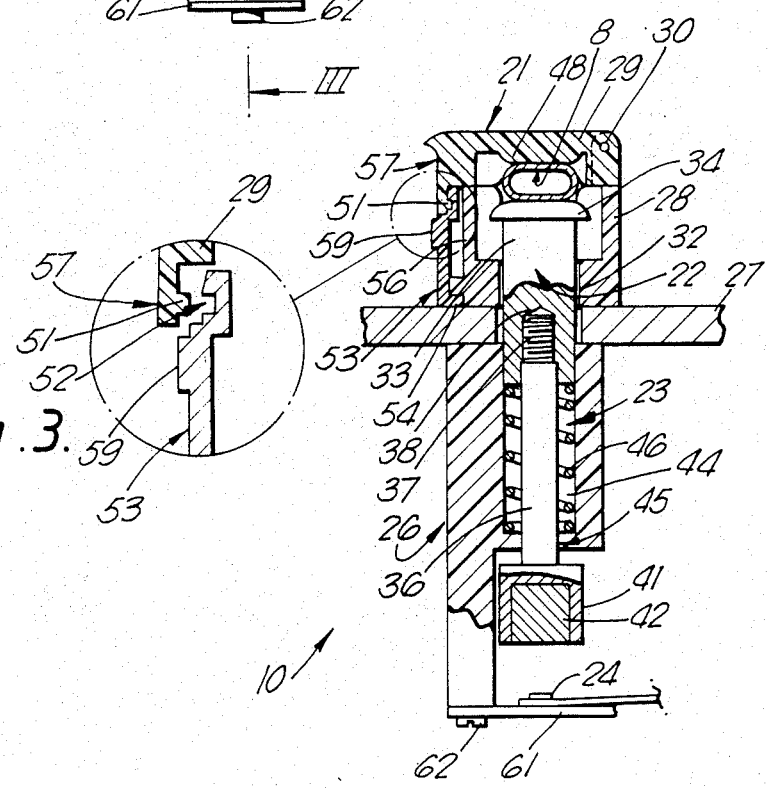
Fig. 2.
Fig. 3.

FIG. 4A
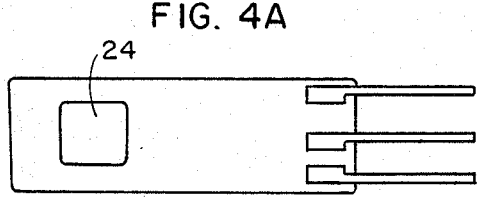
FIG. 4B
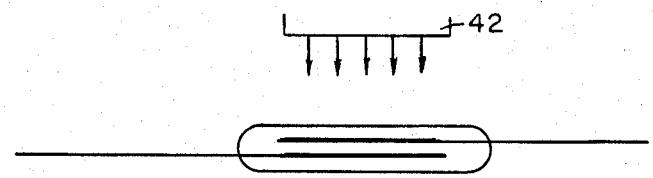
FIG. 5
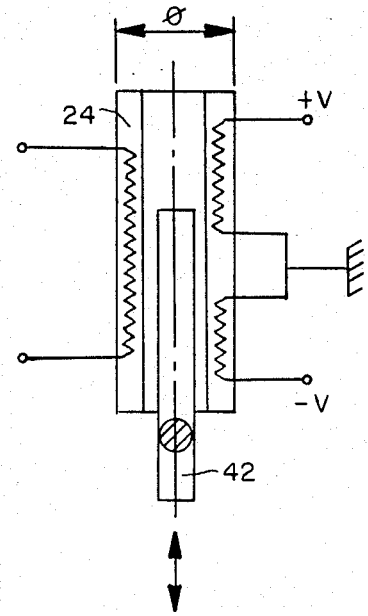

PERISTALTIC PUMP PROVIDED WITH A PRESSURE MEASUREMENT DEVICE

FIELD OF THE INVENTION

The present invention concerns an apparatus for circulating a liquid along a tubular line. In particular, such a liquid may be blood which is flowing in an extracorporeal circulation, for instance, to be purified by a dialysis operation.

PRIOR ART

The apparatus to which the present invention relates is of the type essentially comprising a peristaltic pump provided with a rotor which is acting by means of rollers on the external surface of an elastically deformable tube disposed in series with a tubular extracorporeal line for the blood and comprising, moreover, a device capable of providing an indication of the pressure of the blood which is flowing upstream from the peristaltic pump itself.

In general, this kind of apparatus comprises a tubular reservoir frequently called a pulse damper and made of an elastically deformable material which is connected in series to the extracorporeal blood line and which, in operation, is fitted inside a body constituted by a receptacle closed at its upper portion by a lid. The apparatus, moreover, comprises a micro-switch mounted on the bottom wall of the receptacle in order to detect the deformations induced by the blood pressure, and a screw carried by the lid which can be manipulated by the operator in order partially to deform the reservoir and thus to make it possible to predetermine an intervention threshold for the micro-switch.

It has been observed that the type of apparatus described above has many drawbacks deriving from the use of this reservoir. In fact, the reservoir contains, in operation, a quantity of blood representing a significant percentage of the extracorporeal line capacity and this entails a high inertia level, the response time between the pressure variations and their detection often being too long. For practical reasons of manufacture, the walls of the reservoir cannot be made of a material having a high degree of elasticity and this detracts from the sensitivity of the device. The system of regulating the intervention threshold by means of the above mentioned screw necessitates an adaptation of the structure of the reservoir which affects the sensitivity value and requires the operator's intervention for readjusting the intervention threshold each time a new line is used since the reservoir can only be removed after the screw carried by the lid has been unscrewed. The adoption of the reservoir entails very pronounced variations in cross-section of the blood flow flowing in the extracorporeal line because the cross-section of the line is considerably smaller than that of the reservoir.

Such variations in cross-section, apart from making it possible for air to be drawn in at the junction of the reservoir and of the line, also produce a turbulent motion of the blood which can damage it by producing, for instance, a haemolysis of the red blood cells. Finally, it is appropriate to note that the reservoir is always a component which has to be manufactured and assembled, by bonding, in series in the extracorporeal blood line and that this entails considerable costs of manufacture and labour.

OBJECT OF THE INVENTION

It is an object of the present invention to provide apparatus for circulating a liquid, for instance blood, along a tubular line and which avoids the drawbacks presented by the known types of such apparatus set out above.

SUMMARY OF THE INVENTION

This object is achieved by the present invention which concerns an apparatus for circulating a liquid along a tubular line with a peristaltic pump having a rotor which is acting by means of rollers on the external surface of an elastically deformable tube placed in series into the said tubular line and with a device capable of supplying the pressure values of the liquid flowing in the said line ahead of the said pump. It is characterised in that it comprises:
  a reference element and a movable element between which it is possible to interpose a section of the said tube which is not subjected to the action of the said rollers;
  elastic means which transmit to the said movable element a thrust being exerted towards the said reference element and in a radial direction to the said tube section; and
  measurement means which note the relative position taken by the said movable element in relation to the said referene element and which emit a corresponding electric signal, depending on the deformation of the said tube section, caused in operation by the pressure of the said liquid.

BRIEF DESCRIPTION OF THE DRAWINGS

For a better understanding of the present invention, there will now be described a preferred embodiment merely by way of a non-restrictive example and with reference to the attached drawings wherein:
FIG. 2 is an elevational view on an enlarged scale of a portion of FIG. 1;
FIG. 3 is a cross-sectional view along line III—III of FIG. 2;
and
  FIG. 4A is a side view of a Hall effect transducer;
and
  FIG. 4B is a top plan view of a Hall effect transducer;
FIG. 5 is a schematic of a magnetic action switch electromagnetic transducer;
FIG. 6 is a schematic of a differential transformer.

DESCRIPTION OF THE PREFERRED EMBODIMENT

Figure 1:
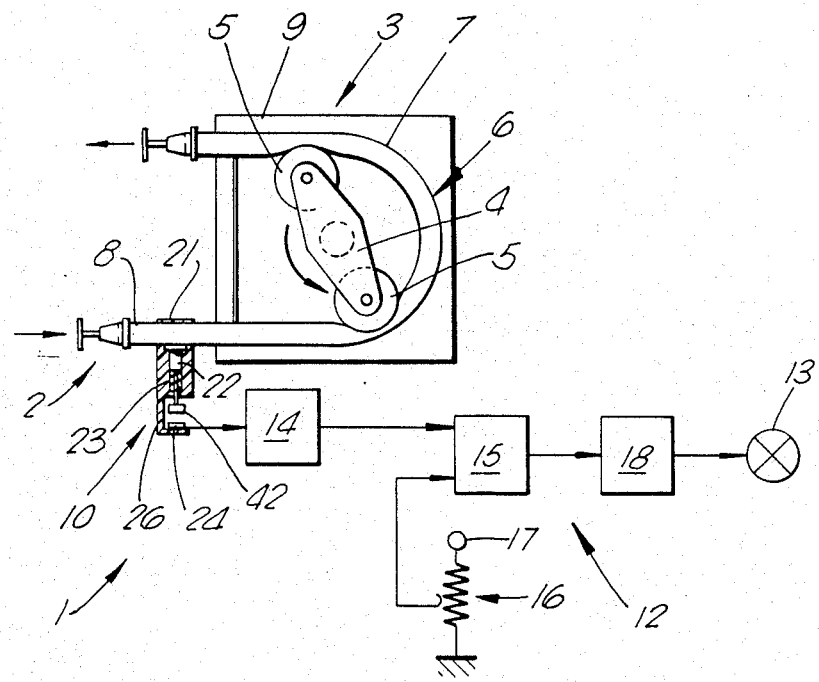
FIG. 1 is a schematic and partly cross-sectional view of an apparatus according to the present invention.
Figure 7:
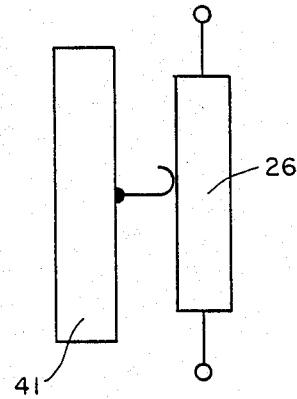
FIG. 7 is a schematic of a potentiometer type transducer.
Figure 8:
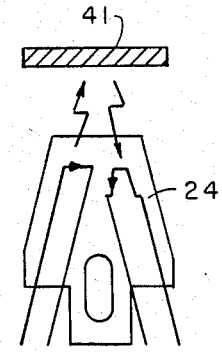
FIG. 8 is a schematic of an opto electronic type transducer.

Referring to FIG. 1 in particular there will be seen apparatus 1 for circulating a liquid along a tubular line 2. Apparatus 1 essentially comprises a peristaltic pump 3 provided with a rotor 4 having rollers 5 which act on the external surface of a first section 7 of a tube 6 formed of an elastically deformable material such as, for example, a plasticised polyvinyl chloride (PVC) and placed in series along the tubular line 2 mentioned above. Apparatus 1 comprises, moreover, a device 10 which is disposed externally of a second section 8 of tube 6 which extends outside the bowl shaped body 9 of the peristaltic pump 3.

As will be described in greater detail with reference to FIGS. 2 and 3, the device 10 is capable of emitting an electric signal depending on the deformation induced, in section 8 of the tube 6 in use, by the effect of the pressure of the liquid flowing within the portion of the tubular line 2 disposed ahead of the peristaltic pump 3.

Apparatus 1 finally comprises an electric circuit generally indicated by reference 12 to compare the electric signal emitted by the device 10 with an adjustable reference signal with the object of giving an alarm signal to a lamp 13 when the divergence between these two signals exceeds predetermined safety limits.

More particularly, the circuit 12 comprises an amplifier 14 which receives the electric signal emitted by the device 10 and which delivers such a signal, suitably amplified, to the first input of a comparator circuit 15 whose second input receives the above mentioned adjustable signal supplied by the slide contact of a potentiometer 16 whose opposed ends are respectively connected to the frame and to a power source of a known type connected to a terminal 17. The output of the comparator circuit 15 is finally connected, by means of an additional amplifier 18, to the signalling lamp 13.

The structure of device 10 will now be described by referring more particularly to FIGS. 1 and 3. Such a device essentially comprises (a) a reference element 21 and a movable element 22 between which the section 8 of the above mentioned tube 6 can be interposed; (b) elastic means 23 transmitting to the movable element 22 a thrust towards the reference element 21 in a radial direction in relation to the section 8 of the tube 6; and (c) measurement means 24 which detect the relative position of the movable element 22 in relation to the reference element 21 and which consequently emit the electric signal used in circuit 12.

More particularly, the device 10 includes a tubular support 26 joined to a channel shaped element 28 by means of screws 25 which pass through holes (not shown) in a plate 27 which also supports the body 9 of the peristaltic pump 3. The channel shaped element 28 forming a receptacle is closed at its upper portion by a lid 29 which constitutes said reference element 21 and which can rotate around a pivot pin 30. The bowl shaped element 28 has, at its base, a hole 32 which axially slidably receives the above mentioned movable element 22.

The movable element is a piston having an upper cylindrical portion 33 with a diameter which is slightly smaller than the diameter of the above mentioned hole 32 and having a head 34 intended to cooperate, in use, with the external surface of tube section 8 of the deformable elastic tube 6. The surface of the head 34 opposite the tube section 8 is flat with an essentially spherical surface at the periphery. The movable element 22 has, moreover, a lower cylindrical portion 36 coaxial with the upper portion 33 but having a smaller diameter. The lower portion 36 has a threaded end 37 engaged in a corresponding tapped hole 38 arranged in the upper portion 33. On the end remote from its end 37, the lower cylindrical portion 36 carries a head 41 forming a receptacle within which is accommodated a permanent magnet 42 capable of acting on the said measurement means 24 as will be described below.

The tubular body 26 of the device 10 defines a cylindrical chamber 44 open at its lower portion at a hole (45) which slidably receives the lower cylindrical portion 36 of the movable element 22. The internal diameter of the chamber 44 is slightly greater than the diameter of the cylindrical portion 33; the chamber 44 thus performs a guiding function for the axial displacements of this cylindrical element 33, and it receives a coil spring 46 coaxial with the smaller diameter cylindrical element 36 in order to transmit to the upper cylindrical portion 33 the above mentioned thrust towards the reference element 21 and radially in relation to the section 8 of the tube 6. This section 8 is thus elastically compressed by the spring 46 which, during operation of the pump, deforms the section 8 indicated in FIG. 3, pressed between, on one side, the flat and circular upper surface of head 34 of the upper cylindrical portion 33 of the movable element 22 and, on the opposed side, a corresponding flat circular surface of a relief 48 on the inwardly facing part of the body of the lid 29.

The connection between the lid 29 and the corresponding box shaped part 28 is effected by not only the pin 30 but also by the catch-engagement of a tooth 51 of the lid 29 with a corresponding cavity 52 in the end of an elastically deformable element 53 and joined at its base to the channel-shaped element 28. More particularly, the connection between the deformable element 53 and the channel-shaped part 28 is produced by forcing the dovetail-shaped base 54 of the deformable element 53 into a cavity at the periphery of the bottom wall of the channel of element 28. In conformity with the elastically deformable element 53, the lateral wall of the channel-shaped receptacle 28 has an essentially rectangular seat designated by reference 56 so as to accommodate practically the whole of the deformable element 53, this being arranged so that the element 53 is essentially located in the same plane as the corresponding lateral surface 57 of the lid 29.

It will finally be observed that near the cavity 52 and the part facing it on the outside, the element 53 has a cylindrical relief 59 whose purpose is to indicate to the user the most convenient region for exerting pressure on the deformable element 53 to disengage the tooth 51 from the cavity 52 and hence to open the lid 29.

The measurement means 24 are supported by a cantilever 61 joined to the body 26 of the device 10 by means of a screw 62. Such measurement means are thus disposed opposite the permanent magnet 42 and coaxially with it and they are capable of emitting an electric signal depending on the intensity of the magnetic field in which they are placed, which electric signal obviously depends on the distance between magnet 42 and the measurement means 24. Preferably these measurement means comprise a "Hall" effect transducer.

The operation of apparatus 1 is as follows. When positioning the extracorporeal blood line, the section 8 of the elastically deformable tube 6 is situated on the side of the peristaltic pump 3 at the part which will be subjected to suction under the effect of rotation of rotor 4. Then the section 8 is simply introduced within the channel-shaped part 28 and the lid 29 is closed by pressure applied at the part remote from the pivot pin 30. In this way, the tooth 51 causes the deformable element 53 to buckle elastically inwards until it occupies the corresponding cavity. In these conditions the section 8 is disposed between the lid 29 and the flat head 34 of the movable element 22 and it is moreover subjected to the radial thrust which it receives from spring 46.

Under normal conditions, the peristaltic pump replaces the flow of the liquid along line 2 by drawing it from the portion where the section 8 is situated and by driving it on into the opposite portion of tube 6. If there is an obstruction of some importance along line 2 ahead of the peristaltic pump 3 the pressure of the liquid contained inside line 2 itself will decrease and in particular also within the section 8. Because the section 8 is made of a particularly deformable material, it is radially deformed and the action of the spring 46 has the effect of keeping the surface of head 34 in contact with the corresponding surface of the section 8 consequently increasing the distance between the magnet 42 and the detector 24. As has already been stated, the electric signal emitted by the detector 24 depends on the value of the magnetic field to which it is exposed; in this specific case, it is subjected to a reduction in amplitude. Such an electric signal, after having been amplified by amplifier 14, is compared by the comparator 15 with the reference signal transmitted by the sliding contact of the potentiometer 16 and, if the divergence between the two signals exceeds predetermined limits, the comparator circuit 15 emits an alarm signal which illuminates the lamp 13 by means of amplifier 18. The adjustment of the intervention threshold in the comparator circuit 15 can simply be effected by manipulating the sliding contact of the potentiometer 16 and by adjusting the contact until the desired threshold value is obtained.

From an examination of the characteristics of the apparatus 1 described above, its advantages will be quite clearly apparent, especially in the case where the liquid to be pumped is blood. In fact, the quantity of blood used for controlling the pressure is now distinctly less than that contained in the reservoirs which have been used previously, because it is limited to that contained in the section 8 of the deformable tube 6. This entails a lower inertia, which makes it possible to have a rapid response with immediate signalling of deformations of the section 8 induced by pressure variations in excess of admissible limits.

A rapid resumption of normal working conditions is also obtained thanks to either the considerable elasticity of the walls of section 8 or the smaller quantity of blood circulating between the inlet of pump 6 and the zone of vascular access of the extracorporeal blood line 2. The sensitivity of the device 10 is substantially improved as a result of the high elasticity of the walls of section 8 and it is not affected by the threshold adjustments which are effected electronically.

Moreover, the operations of positioning and withdrawing the extracorporeal blood line 2 are simplified still further, because it is no longer necessary to repeat the calibration every time the tube is changed by screwing and unscrewing the screw in the lid as in the known type of apparatus. It follows that there are no undesirable changes in cross-section of the tubular conduit, apart from those required by the connection between line 2 and the tube 6.

The above mentioned known problems, due to an imperfect seal of the junctions between the reservoir and the line in the prior art pump, no longer subsist, nor do the difficulties (haemolysis etc. . . . ) due to the turbulent blood flow. Finally, it is obvious that since the line no longer requires the existence of a reservoir the system is obviously simplified and is cheaper as regards costs of manufacture and of labour.

Finally, it is clear that various variants and modifications may be made to the apparatus described above, without thereby departing from the scope of the present invention.

For instance, as shown in FIGS. 4 to 8 the measurement means or detector 24 could be suitably built by means of a magnetic Reed switch in which case it could be mounted on a cross member or cantilever whose position in relation to magnet 42 could be axially adjusted in an accurate and precise way. The transducer 24 and magnet 42 could also be replaced by a differential transformer, or by a potentiometer type of transducer, or yet again by an opto electronic type of position transducer which could comprise, for example, an optical reflection device in order to obtain embodiments equivalent to those described above.

Another embodiment could employ an analog type indicating instrument immediately at the output of the amplifier circuit 14, thereby replacing the comparator 15, potentiometer 16, amplifier 18 and the signalling lamp 13. However, in such a case the indications supplied by such an instrument would be monitored at regular intervals.

We claim:
1. In apparatus for sucking a liquid in a tubular conduit comprising:
   (a) an elasticity deformable tube in series with said tubular conduit;
   (b) a peristaltic pump including a rotor with rollers which act on the external surface of said elastically deformable tube, and
   (c) means detecting the negative pressure of the liquid sucked in the said elastically deformable tube ahead of the said pump, the improvement wherein said negative pressure detecting means comprise:
   (d) a fixed element adapted to define a reference for a section of said elastically deformable tube which is not subjected to the action of said rollers;
   (e) a movable element opposite said fixed element to define a gap in which it is possible to place a section of the said elastically deformable tube; said movable element being adapted to move in a radial direction to said section of the tube;
   (f) means adapted to maintain said movable element in contact with said section of said elastically deformable tube and to allow its movement in said radial direction;
   (g) means responsive to the relative positions of said movable element and said fixed element, for emitting an electric signal depending on the deformation of said section of the tube caused in operation of the pump by the pressure of the said pumped liquid;
   (h) means defining a receptable to receive said section of the elastically deformable tube, a base to said receptacle and means defining a hole in said base; wherein said fixed element is the lid of said receptacle and wherein said movable element is a piston sliding axially within said hole in the base of the said receptacle, said piston facing towards said lid; and
   (i) detent means for connecting said lid and said receptacle, comprising a tooth on the lid and means defining a corresponding cavity in an elastically deformable element joined to said receptacle.

2. In apparatus for sucking a liquid in a tubular conduit comprising:
   (a) an elasticity deformable tube in series with said tubular conduit;
   (b) a peristaltic pump including a rotor with rollers which act on the external surface of said elastically deformable tube, and
   (c) means detecting the negative pressure of the liquid sucked in the said elastically deformable tube ahead of the said pump, the improvement wherein said negative pressure detecting means comprise:

(d) a fixed element adapted to define a reference for a section of said elastically deformable tube which is not subjected to the action of said rollers;

(e) a movable element opposite said fixed element to define a gap in which it is possible to place a section of the said elastically deformable tube; said movable element being adapted to move in a radial direction to said movable element to the tube;

(f) elastic means adapted to maintain said movable element in contact with said section of said elastically deformable tube and to allow its movement in said radial direction;

(g) means responsive to the relative positions of said movable element and said fixed element, for emitting an electric signal depending on the deformation of said section of the tube caused in operation of the pump by the pressure of the said pumped liquid;

(h) means defining a receptacle to receive said section of the elastically deformable tube, a base to said receptacle and means defining a hole in said base; wherein said fixed element is the lid of said receptacle and wherein said movable element is a piston sliding axially within said hole in the base of the said receptacle, said piston facing towards said lid, and (i) said elastic means act in an axial direction in relation to said piston, and include a lower cylindrical element associated with said piston, the relative axial position of said lower element being detected by the position-responsive means, said lower cylindrical element provided at one end with a permanent magnet, and wherein said position-responsive means comprise at least one electromagnetic type transducer.

3. Apparatus according to claim 2 wherein said electromagnetic transducer is a Hall effect transducer.

4. Apparatus according to claim 2 wherein said electromagnetic transducer is a magnetic action switch.

* * * * *